United States Patent [19]

Limet et al.

[11] 4,253,844

[45] Mar. 3, 1981

[54] INSOLUBILIZED PROTEINS AND IMMUNOASSAYS UTILIZING THEM

[75] Inventors: Joseph Limet, Marchin; Cesar L. Cambiaso, Kraainem; Claude H. Moussebois; Pierre L. Masson, both of Brussels, all of Belgium

[73] Assignee: Technicon Instruments Corporation, Tarrytown, N.Y.

[21] Appl. No.: 5,260

[22] Filed: Jan. 22, 1979

[30] Foreign Application Priority Data

Jan. 26, 1978 [GB] United Kingdom ................. 3238/78

[51] Int. Cl.$^3$ ............................................. G01N 33/54
[52] U.S. Cl. ................................. 23/230 B; 252/408; 424/12; 435/177; 435/180; 435/181
[58] Field of Search .................. 23/230 B; 424/1, 12; 435/177, 180, 181; 252/408

[56] References Cited

U.S. PATENT DOCUMENTS

| | | | |
|---|---|---|---|
| 3,639,558 | 2/1972 | Csizmas | 435/177 X |
| 4,070,246 | 1/1978 | Kennedy | 435/177 X |
| 4,081,244 | 3/1978 | Polito | 23/230 B X |
| 4,108,976 | 8/1978 | Reese | 424/1 |
| 4,140,662 | 2/1979 | Reckel | 435/181 X |
| 4,175,073 | 11/1979 | Carlsson | 435/180 X |
| 4,181,636 | 1/1980 | Fischer | 435/181 X |

*Primary Examiner*—Sidney Marantz
*Attorney, Agent, or Firm*—S. P. Tedesco

[57] ABSTRACT

Insolublized antibodies, F(ab')$_2$ fragments thereof and protein antigens are made by coupling to a water-insoluble substrate using a bridging agent which covalently binds to sulphur atoms in antibody, fragment or protein rather than to free amino groups therein. This is preferably effected by using a chloracetyl-terminated bridging agent. Immunoassays utilizing these insolubilized reagents are described. One novel class of bridging agents comprising anhydride and monochloracetyl end groups, which is useful for making the said reagents, is also disclosed.

23 Claims, No Drawings

INSOLUBILIZED PROTEINS AND IMMUNOASSAYS UTILIZING THEM

This invention is concerned with immunoassays and, more particularly, with immunoassays involving insolubilised antibodies or protein antigens as reagents, and with such reagents, a method of making them, and certain bridging substances useful therefor.

It is known to use insolubilised antibodies and antigens as reagents in various immunoassays. These reagents are usually prepared either by absorbing the antigen or antibody on a water-insoluble support, or by covalently linking the antibody or antigen to a water-insoluble support using a bifunctional bridging group. Among the commonest bifunctional bridging groups are dialdehydes such as glutaraldehyde. Such bridging groups react readily with free amino groups in the antibody or protein antigen.

Many immunoassay procedures involving insolubilised antibody or protein antigen involve the well known immunospecific reaction between a particular antibody (or antigen) and its corresponding antigen (or antibody). It is known that there are local active sites in the protein molecules which are specific to such reactions, and that there are free amino groups in or adjacent these active sites. When an antibody (or protein antigen) is insolubilised by covalent bridging according to standard techniques, therefore, the active sites become blocked to some extent. This reduces the activity of the protein in any subsequent immunospecific reaction, e.g. in an immunoassay, and this is disadvantageous.

We have now found a way of overcoming or reducing this disadvantage. In particular, we have found that antibodies and protein antigens can be insolubilised by covalently binding them to a water-insoluble substrate, using as a bridging agent a substance which will link to the sulphur atoms present in the protein, in preference to amino groups therein.

According to one aspect of the invention, therefore, there is provided a reagent for use in immunoassays involving an immunospecific reaction between an antibody and an antigen, which comprises a reagent for use in immunoassays which comprises a protein antigen, an antibody or the F(ab')$_2$ fragments of an antibody, covalently bonded to a water-insoluble substrate by a bridging group which is directly linked to sulphur atoms in the said antigen, antibody or fragments.

In another aspect, the invention provides a method of immunoassay which includes the step of effecting an immunospecific reaction between an antigen and an antibody or F(ab')$_2$ fragment thereof, wherein there is used a reagent of the invention.

In a further aspect, the invention provides a method of making a reagent of the invention which comprises reacting a protein antigen or an antibody or the F(ab')$_2$ fragments thereof, with a bridging reagent to covalently link the bridging agent directly to sulphur atoms in the said antigen, antibody or fragments, and wherein before or after said reaction the bridging agents is covalently bonded to a water-insoluble substrate.

Antibody immunoglobulins comprise a number of polypeptide chains linked at intervals by disulphide bonds. The chains themselves may also contain disulphide groups. In a preferred aspect of this invention, the disulphide links are subjected to mild reduction to form sulphhydryl groups —SH, and these are then reacted with one function of a bifunctional bridging agent. The said one function is one which will react with —SH groups in preference to free amino groups. A preferred such function is a chloroacetyl group, for example monochloroacetyl —CO—CH$_2$—Cl.

The other reactive function of the bifunctional bridging agent reacts with the water-insoluble substrate (to which the antibody or protein antigen is to be bound). The nature of this reactive function will depend on the nature of the substrate chosen, and many suitable substrates (and functional groups reactive therewith) are known in the art. The substrate may, for example, be in sheet form or in the form of a tube. In the latter case, the antigen or antibody can be immobilised on the inside or the outside of the tube, or both. More usually, however, the substrate will be in particulate form and the reagents of the invention may then, for example, comprise the particles in suspension in an aqueous fluid which may suitably include a buffer. In one preferred arrangement, the particulate substrate is magnetically attractable so that it can be readily separated from a mixture by the application of a magnetic field. The use of particulate materials in immunoassay procedures is well known. A particularly preferred particulate substrate is latex particles.

The nature of the material of which the substrate is composed is not critical except that it must be capable of reacting with one end or part of the bridging agent. Synthetic polymeric materials which are water-insoluble can be used to form the substrate and usually such substrates will be provided with a reactive coating, for example a protein coating. A typical protein useful for this purpose is albumin. In such cases, the bridging group will contain, as one function, a group which will readily react with albumin. Whilst there are several such groups known, according to a preferred feature of this invention we use an anhydride, most preferably of the formula:

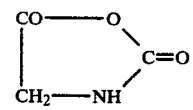

Such a group reacts readily with the free amino groups of a protein such as albumin.

In order to make a reagent of the invention in which an antibody or protein antigen is covalently bound to a protein such as albumin, we prefer to use a bifunctional bridging substance having at one end the chloroacetyl group I and at the other end the anhydride group II. A highly preferred class of such bridging agent has the general formula:

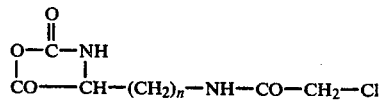

where n is an integer from 1 to 10, preferably 4. These compounds are novel per se and form a further aspect of the present invention. The compound of formula III above in which n=4 is hereinafter referred to as "NCA".

When, as in NCA and the other compounds of formula III, the bridging agent contains a functional group which will react readily with protein amino groups, it is important to make sure that the said functional group does not react with free amino groups in the antigen, antibody or F(ab')$_2$ fragments. This may be ensured by, for example, first reacting the bridging agent with the water-insoluble support, and only thereafter bringing it into contact with the immunoglobulin antibody or protein antigen.

There is now described one example of a procedure for preparing a reagent of the invention. Latex particles are coated with albumin (or another protein or polypeptide such as lactoferrin), the albumin being absorbed on the latex particles. In the case of a coating containing sulphur groups which might react with the bridging groups, e.g. in the case of an albumin coating, the coating material is alkylated (before or after formation of the coating) to destroy or inactivate such groups. The albumin-coated particles are then incubated with NCA for about 24 hours at a netural pH (e.g. 7.1) and the anhydride groups of the NCA react with the amino groups on the albumin. (Alternatively, the NCA may first be coupled to the alkylated albumin and the resulting compound coated on the particles.)

Antibody is subjected to mild reduction (for example with dithiothreitol) to produce a sulphhydryl groups therein. It is then mixed with the latex-albumin-NCA particles, and incubated at room temperature for 36 hours. The antibody reacts with the chloroacetyl group in the NCA and is thus covalently linked (via the NCA) to the albumin.

Of the various antibody immunoglobulins, IgG is the most common. As is known, IgG molecules tend to assume the shape of a "Y", the two upper limbs (F(ab')$_2$ portions) containing at their outer ends the antigen binding sites, and the lower limb (F(c) portion) containing inter alia sites which react with RF and C1q, for example. The area at which the three limbs of the Y intersect is called the hinge area or region. At this region, there are disulphide links between adjacent polypeptide chains and it is, we believe, these links with which the preferred bridging agents of the invention react. It will be seen, therefore, that the bridging group does not interfere with the antigen binding sites on the F(ab')$_2$ portions of the molecule.

It is preferred according to the invention to use a bridging group which contains a chain of at least 5 atoms length (more preferably bridging agents of formula III in which n is 4 or above) in order to dispose the antibody (e.g. IgG) or antigen some distance from the substrate surface to which it is linked. This tends to make the antigen or antibody more accessible to reaction than in prior art procedures using, for example, cyanogen bromide or glutaraldehyde as a bridging agent. Thus, we have found that the activity of an antibody in a reagent of the invention using NCA is many times greater than when the same antibody is absorbed directly on the substrate. For example, in an agglutination assay using latex-BSA-NCA-antibody and antigen, the sensitivity of the test was about 50 times greater than when the antibody was merely absorbed directly on the latex (in this case, the antigen was horse ferritin and the antibody was rabbit antiferritin. "BSA" means bovine serum albumin.

In our co-pending U.K. patent application Ser. No. 3237/78 (Docket 2089F), we have described a method of immunoassay in which there is used, in place of whole immunoglobulin, the F(ab')$_2$ fragments thereof. The reagents of the present invention may include, in place of antibody, F(ab')$_2$ fragments thereof. Such reagents can be made in a highly advantageous manner, using the compounds of formula III, preferably NCA, as follows. After forming (as described in detail above) the latex-albumin-NCA-antibody particles (in which, for example, the antibody is IgG), the particles are digested with pepsin. In the result, there is formed latex-albumin-NCA-F(ab')$_2$, i.e. the F(c) fragment is no longer present. Most preferably, reagents of the invention including F(ab')$_2$ fragments of IgG are substantially free from the corresponding whole IgG and F(c) fragments. Reference should be made to our said copending application for further details of the use of F(ab')$_2$ fragments in immunoassays.

The reagents of the invention can be used in a wide variety of immunoassay procedures, as will be clear to those skilled in the art. A method of the invention for the assay of an antigen in a fluid comprises the steps of:

(a) forming a mixture of a sample of the fluid with a reagent of the invention comprising an antibody or F(ab')$_2$ fragment thereof, the antibody being such as will bind with the antigen under assay;

(b) incubating the mixture to allow reaction to occur; and (c) assaying the mixture to determine the extent of said reaction and thereby, the amount of antigen in the fluid sample.

When a reagent of the invention comprising F(ab')$_2$ fragments is used, preferably the reaction mixture is substantially free from the corresponding immunoglubulin and F(c) fragments.

A similar method may be used to assay an antibody in a fluid, using a corresponding protein antigen to bind therewith.

One highly preferred assay of the invention is the latex agglutination assay. In this assay, there is used a reagent in the form of a latex particle suspension, the particles agglutinating upon reaction with the antigen or antibody under assay. The extent of the reaction is determined by observation of the amount of agglutination, from which the amount of antigen or antibody in the sample fluid under assay can be determined. Most preferably, the amount of agglutination is determined by selectively counting the unagglutinated latex particles remaining in the reaction mixture.

In another preferred assay of the invention, the reagent comprises particles which are then separated from the reaction mixture and either the separated particles, or the remaining mixture (or possibly both) are analysed to determine the amount of antigen or antibody under assay. Preferably, the particles are magnetically attractable and are separated by the use of a magnetic field. The use of magnetic particles in this way is described in our Belgian Pat. No. 852,327 to which reference should be made for further details.

The methods of assay of the invention can be effected on a variety of fluids but, most usually, human body fluids such as blood, blood serum or plasma, will be assayed.

The methods of the invention may be effected on a discrete manual basis or in an automated manner, e.g. by the so-called continuous flow techniques in which individual segments of reaction mixture are passed along the conduit, separated by an inert segment (e.g. air) and, if desired, a wash liquid segment. This is described in U.S. Pat. No. 2,797,149 to which reference should be made for further details.

In general, particulate reagents of the invention may be of any convenient particle size. For most purposes, a size of from about 1 to 20μ is appropriate. Especially (but not only) in the case of use in continuous flow techniques, the specific gravity of the particles should preferably be from about 1.4 to 3.2 (or at least close to that of the reaction mixture liquid) to avoid undue floating or settling of the particles in the flowing liquid reaction mixture.

In order that the invention may be more fully understood, the following Examples are given by way of illustration only.

EXAMPLE 1

A serum or plasma sample containing antigen to be measured is mixed with a suspension of latex particles on to which are bound antibodies to the antigen. The mixture is passed into a conduit segmented with air. The mixture is held in a time-delay coil, vibrated at 50 Hz for 15-20 minutes to accelerate strong agglutination. The latex particles are diluted successively 1:80 and 1:80 to give a final dilution of 1:64000. The particles then pass through an AutoCounter specially modified electronically to reject all non-monomer particles.

The decrease in the number of monomers is directly proportional to the concentration of antigen present.

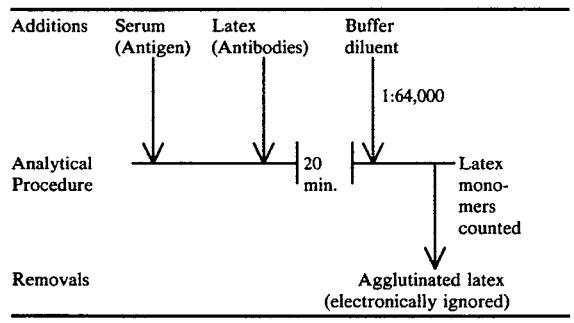

EXAMPLE 2

REAGENT PREPARATION

Latex Particles

Dow 0.794 micron diameter, S.D. 0.044 micron—No. 41943, Serva, Feinbiochemica, D-6900 Heidelberg 1, Germany (10% suspension).

Alkylated bovine serum albumin

Alkylated bovine serum albumin (BSA) is prepared as follows. A solution of BSA in phosphate buffer (0.1 M, pH 8.5) is mixed with a five-molar excess of dithiothreitol (DTT) and left for 1 hour at 37° C. The DTT reduces the BSA. There is then added iodoacetic acid in an amount 10 times in excess of the DTT. After two hours at room temperature, the BSA is separated, and the alkaline portion is equilibrated on Sephadex G25 in a phosphate buffer solution (0.1 M, pH 7.2).

Coupling NCA to BSA

The alkylated BSA in a phosphate buffer (0.1 M, pH 7.2) is incubated with one-seventh of its weight of NCA at 4° C. overnight. The protein may be used directly after dialysis at pH 7, or lyophilised after dialysis into ammonium bicarbonate.

Coupling BSA/NCA to latex 0.4 ml of phosphate buffer (pH 7.1) was mixed in a glass tube with 250 mg of BSA/NCA in phosphate buffer and 50 ml of the 10% latex suspension. Just before use, the latex to be treated is washed twice with buffer at pH 9.6 (0.1 M) and is then re-suspended in the same buffer solution.

Alkylation of IgG

Sheep antiferritin antiserum was mildly reduced in DTT as follows. The IgG was incubated for 1 hour in the presence of a 2-molar excess of DTT in a solution of 0.1 M bicarbonate at pH 8.5.

Latex-BSA/NCA-IgG 50 ml of 10% latex-BSA/NCA suspension is mixed with 1 mg of reduced IgG. The mixture is purged with $N_2$ for 30 minutes and then sealed under less than 5 mm Hg pressure in a glass tube and kept in the dark. Before use, it is washed twice with 1 ml of buffer comprising 0.17 M NaCl, 0.1 M glycine (pH 9.2), and 0.05% Tween 20, and then resuspended in 1% BSA in the same buffer (0.27 M) but in the absence of Tween 20.

ASSAY

The agglutination assay for ferritin in serum is carried out as described above. Sera of 27 different ferritin contents were assayed, each serum being run several times. The sera were also assayed by the RAMCO radioimmunoassay technique. The coefficient of correlation between the two assay methods was 0.92. The samples of sera were run at a dilution of 20:1 and had a normal range of 20-300 micrograms ferritin per liter.

EXAMPLE 3

PREPARATION OF NCA

At 25° C., 442 mg ε-N-chloroacetyl-α-carbobenzoxy-L-lysine (0.00123 moles) is dissolved in 1 ml of di-oxene. The solution is mixed with 80 ml of a mixture of benzene and ethyl ether (1 vol. to 1 vol.), and the resulting mixture contacted with 256 milligrams of $PCl_5$ at 25° C. for 3 hours, in a dry atmosphere.

The solvent is evaporated at 25° C. under a pressure of 30 millimeters over about 2 hours in a dry atmosphere, and the liquid obtained is washed twice with 10 mls of ethyl ether. The ether is removed and the residue is taken to dryness. It is then dissolved again in 5 ml of ethyl acetate and re-precipitated at 4° C. by 20 ml of light petrol ether (boiling fraction 40° C.-60° C.). Analysis of the product:

|  | Theoretical | Found |
| --- | --- | --- |
| CARBON | 43.47 | 43.44 |
| HYDROGEN | 5.27 | 5.31 |
| NITROGEN | 11.26 | 11.27 |

This is the analysis of NCA, i.e.

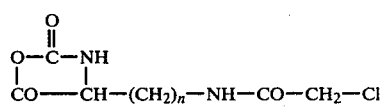

wherein n is 4.

In order to make similar compounds in which n is, for example, greater than 4, a derivative of an χ-amino acid is used comprising a second amine within the long chain, or the appropriate amide is formed with a beta, gamma or delta amino acid. For example:

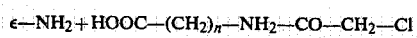

which gives:

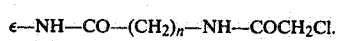

We claim:

1. A reagent for use in immunoassays which comprise a protein antigen, an antibody or the F(ab')$_2$ fragments of an antibody, covalently bonded to a water-in-soluble substrate by a bridging group which is directly linked to sulphur atoms in the said antigen, antibody or fragments, that portion of the bridging group linked directly to the said sulphur atoms being derived from a monochloracetyl group.

2. A reagent according to claim 1 wherein the bridging group contains a chain of at least 5 atoms length to separate spatially the said antigen, antibody or fragment, from the substrate.

3. A reagent according to claim 1, wherein the said antibody is an immunoglobulin G.

4. A reagent according to claim 1, which comprises the F(ab')$_2$ fragments of an immunoglobulin G, and which is substantially free from the said immunoglobulin G and F(c) fragments thereof.

5. A reagent according to claim 1, wherein the substrate comprises a protein to which the said bridging group is directly linked, and wherein that portion of the bridging group which is linked to the protein of the substrate is derived from an anhydride group.

6. A reagent according to claim 5, wherein the bridging group is derived from a compound of the formula

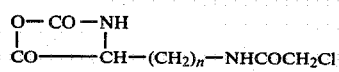

wherein n is an integer from 1 to 10.

7. A reagent according to claim 1, wherein the substrate is in sheet-like form or in the form of a hollow tube, or is a particulate material.

8. A reagent according to claim 7, wherein the substrate is a latex, or is a particulate material which is magnetically attractable.

9. A reagent for use in immunoassays which comprises a water-insoluble particulate material in suspension in a fluid, the particulate material having a protein coating to which is covalently linked the anhydride group of a bridging agent of the formula

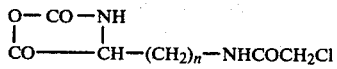

wherein n is from 1 to 10, the chloroacetyl group of said agent being directly bonded to sulphur atoms in an antigen protein, an antibody or the F(ab')$_2$ fragments of an immunoglobulin G antibody.

10. A reagent according to claim 9, wherein in the formula n is 4.

11. A method of immunoassay which includes the step of effecting an immunospecific reaction between an antigen and an antibody or F(ab')$_2$ fragment thereof, wherein there is used a reagent which comprises a protein antigen, an antibody or the F(ab')$_2$ fragments of an antibody, covalently bonded to a water-insoluble substrate by a bridging group which is directly linked to sulphur atoms in the said antigen, antibody or fragments, that portion of said bridging group directly linked to said sulphur atoms being derived from a monochloroacetyl group and that portion of the bridging group bonded to said substrate being derived from an anhydride group.

12. A method according to claim 11 for assaying an antibody in a fluid which comprises the steps of:
(a) forming a mixture of a sample of the fluid with the said reagent comprising a protein antigen which will bind with the antibody under assay;
(b) incubating the mixture to allow reaction to occur; and
(c) assaying the mixture to determine the extent of said reaction and; thereby, the amount of antibody in said fluid sample.

13. A method according to claim 11, wherein the reagent comprises magnetically attractable particles and wherein, after said reaction, the particles are separated from the remainder of the reaction mixture by applying a magnetic field.

14. A method according to claim 11, which is carried out in a continuous flow manner.

15. A method according to claim 11, wherein an antigen or antibody in human serum is assayed.

16. A method according to claim 11 for assaying an antigen in a fluid, which comprises the steps of:
(a) forming a mixture of a sample of the fluid with the said reagent in which the antibody or F(ab')$_2$ fragment thereof is such as will bind with the antigen under assay;
(b) incubating the mixture to allow reaction to occur; and
(c) assaying the mixture to determine the extent of said reaction and thereby, the amount of antigen in the fluid sample.

17. A method according to claim 16 wherein the reagent comprises F(ab')$_2$ fragments, and the reaction mixture is free from the protein antibody from which the fragments have been obtained, and free from the corresponding F(c) fragments.

18. A method according to claim 11 wherein the reagent is in the form of latex particles suspension and wherein said reaction causes agglutination of the said particles, the extent of the said reaction being determined by observation of the amount of agglutination.

19. A method according to claim 18, wherein the amount of agglutination is determined by selectively counting the unagglutinated latex particles remaining in the reaction mixture.

20. A method of making a reagent for use in immunoassays, which comprises reacting a protein antigen or an antibody or the F(ab')$_2$ fragments thereof, with a bridging reagent to covalently link the bridging agent directly to sulphur atoms in the said antigen, antibody or fragments, and wherein before or after said reaction the bridging agent is covalently bonded to a water-insoluble substrate, said bridging agent including a terminal chloracetyl group, said sulphur atoms in the antigen, antibody or F(ab')$_2$ fragments being reduced to sulphhydryl groups, said chloroacetyl group of said bridging agent reacting with the sulphhydryl groups to covalently link the bridging agent to the antigen, antibody or F(ab')$_2$ fragments.

21. A method according to claim 20, wherein the water-insoluble substrate comprises free amino groups, and wherein the bridging agent includes a second terminal group which is reactive towards said free amino groups to covalently link the bridging agent to the said substrate; and wherein the method is so effected that reaction of said secnd terminal group with free amino groups on said antigen, antibody or F(ab')$_2$ fragments does not occur.

22. A method according to claim 20, wherein the bridging agent has the formula

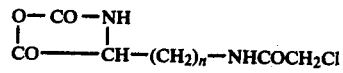

wherein n is an integer from 1 to 10.

23. A method of making a reagent for use in immunoassays, which method comprises preparing a reagent comprising an immunoglobulin G antibody covalently bonded to a water-soluble substrate by a bridging agent, said bridging agent having a terminal chloroacetyl group which is directly linked to sulphur atoms in the said antibody, and subjecting the reagent to digestion with pepsin to free the F(c) fragments.

* * * * *